United States Patent [19]

Thomas et al.

[11] Patent Number: 5,253,654
[45] Date of Patent: Oct. 19, 1993

[54] ORTHOPEDIC WEIGHT MONITOR

[76] Inventors: Berten R. Thomas, 38 N. Pine Cir., Belleair, Fla. 34616; Harry Steinman, 1965 Cove La., Clearwater, Fla. 34624; Stephen D. Alley, 3425 High Bluffs Dr., Largo, Fla. 34640

[21] Appl. No.: 876,481

[22] Filed: Apr. 30, 1992

[51] Int. Cl.⁵ .................................... A61B 51/103
[52] U.S. Cl. .................................. 128/779; 73/172; 340/666
[58] Field of Search ............... 128/774, 779, 782; 73/172, 862.68; 340/573, 666; 364/413.02

[56] References Cited

U.S. PATENT DOCUMENTS

| | | | |
|---|---|---|---|
| 3,702,999 | 11/1972 | Gradisar | 340/573 |
| 4,121,153 | 10/1978 | Levin | 73/172 |
| 4,730,625 | 3/1988 | Fraser et al. | 128/782 |
| 5,042,504 | 8/1991 | Huberti | 128/779 |
| 5,131,399 | 7/1992 | Sciarra | 128/903 |

Primary Examiner—Randy C. Shay
Attorney, Agent, or Firm—Dominik, Stein, Saccocio, Reese, Colitz & Van Der Wall

[57] ABSTRACT

An improved orthopedic weight monitor for detecting weight bearing forces on a lower extremity for orthopedic purposes, comprising in combination: flexible pad shaped for conforming to the bottom of a foot for placement inside of a shoe, cast or splint, the pad having a heel portion positionable beneath the heal of a user; sensor encased within the heel portion of the pad to be located beneath the heel of the user, the sensor comprising a thin, rigid rectangular plate having a foil strain gage coupled therebeneath; electronic module remotely positioned from the sensor to receive signals from the foil sensor; and electrical line extending to exterior of the flexible pad between the foil stain gage and the electronic module.

22 Claims, 6 Drawing Sheets

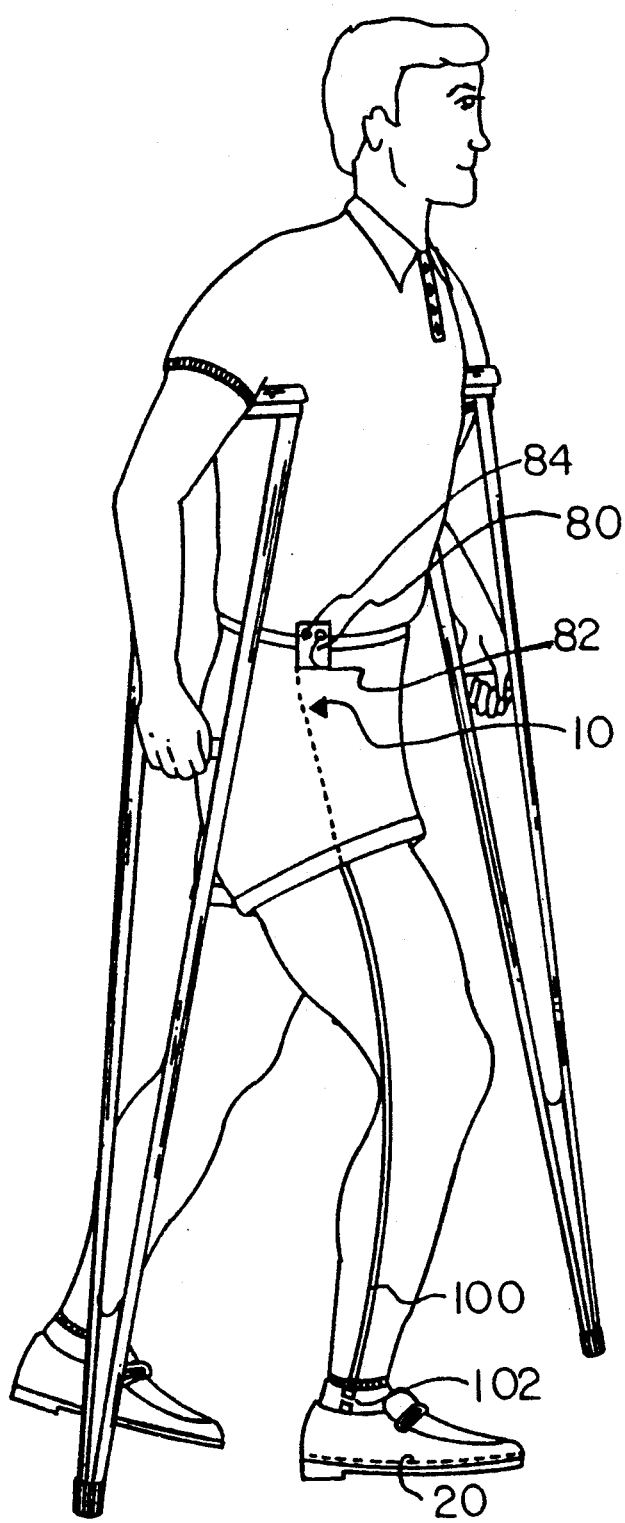
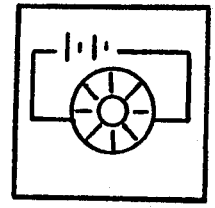
FIG. IA
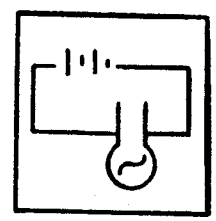
FIG. IB
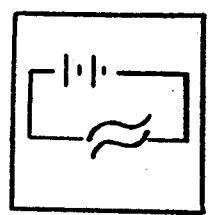
FIG. IC
FIG. I

ORTHOPEDIC WEIGHT MONITOR

BACKGROUND OF THE INVENTION

1. Summary of the Invention

This invention relates to an improved orthopedic weight monitor, and more particularly, to an orthopedic weight monitor having a flexible pad shaped to conform to the inside of a shoe or to be incorporated into a cast or splint with a sensor encased within the heel portion of the pad and a electronic module positioned remotely from the sensor for receiving signals from the sensor by way of an electrical coupling between the sensor and the electronic module.

2. Description of the Background Art

In the field of orthopedic weight monitors, there have been a variety of devices designed to facilitate the detection and/or monitoring of weight bearing on a lower extremity, whether a foot, leg, hip or the like, for medical purposes. A patient who has any kind of medical condition that necessitates restriction of the weight bearing capacity of their lower extremities is doctor instructed not to apply any more than a specific amount of weight to the affected lower extremity until the condition of the extremity has changed. The goal is to help educate the patient, to inform the attending doctor, and to monitor the patient's adherence to the amount of weight applied to the lower extremity. This monitoring device is most beneficial and would have excellent therapeutic benefits.

Commonly, when patients with a lower extremity disability are undergoing rehabilitation training, the amount of weight bearing on the lower extremity in the early stages of treatment is limited. There is an optimum course of progress of weight bearing to yield the most effective and expedient healing of patient suffering from a lower extremity condition. By way of example, patients with fractures, grafts, joint replacements or soft tissue injury should be encouraged to apply moderate pressures to the affected area for encouraging rapid healing. Whereas, excessive pressures on the affected area will adversely effect healing.

Therefore, there exists a variety of reasons why it is medically desirable to determine if any, or at what levels, weight is being born by the affected bone. Historically, patients have been instructed to press down on a scale device to a prescribed load for optimum healing of the patient's injury. Further, the patient is instructed that while walking he should visualize the scale and the amount of effort required to achieve the prescribed scale loading and to apply that same loading while walking to promote proper healing of the affected bone. Unfortunately, the scale method is not an effective method for the patient to judge the proper amount of pressure that should be applied to the affected extremity. There is no form of feedback which is essential to aid the attending physician. Also the scale method only provides static loading input to the patient. The static loading is extremely difficult for the patient to equate to the dynamic loading of the extremity under walking conditions. Furthermore, it can be extremely difficult to reproduce the desired loading on a consistent basis. Finally, many patients have sensation depravation or less than adequate sensations in the lower extremities to adequately equate the results from the scale method to walking conditions.

The present invention is directed to provide for improved devices which detect and monitor weight bearing by feet, legs or hips done in a manner which is safe, secure, clean, economical and aesthetically pleasing.

Throughout the United States steps are being taken to improve upon devices for the detection and monitoring of weight bearing by feet, legs or hips for medical orthopedic purposes. The prior art discloses several types of orthopedic weight monitors. By way of example, U.S. Pat. Nos. 3,702,999 to Gradisar, 4,745,930 to Confer and 4,647,918 to Goforth disclose weight monitoring devises.

Two force sensitive electrical conductors disposed, one each, in predetermined locations beneath the heel and ball of the foot of a user are illustrated in '999. The conductors comprise a pair of flat circular metal plates which are separated by a resilient member. The contacts within the conductor are spaced apart form each other and are of a generally flat circular shape. An elastomeric ring is disposed essentially between the contacts. Therefore, the plates are held apart from each other by the resilient member. Furthermore, the upper plate has a threaded nut secured thereto for engaging a set screw. As force is applied to the conductors, the elastomeric compresses causing the set screw to engage the lower plate to complete an electrical circuit. A flat braided flexible wire extends along the top side of the sole pad and is connected to the top contact within each of the conductors in the toe and heel. A second flat braided flexible wire extends along the bottom side of the sole pad and is connected to the bottom contact within each of the conductors in the heel and toe. The device relies on adjustment of the set screw to vary the amount of force required to complete the electrical circuit. The disclosure teaches a pair of electrical contacts spaced apart from one another by an elastomeric material. The contacts cannot provide a thin profile that is required to facilitate a thin pad or insole to be placed under a patient's foot for optimal performance of the orthopedic weight monitor. The thickness of the mechanical conductors creates a bulky orthopedic monitor which impedes the patient's normal walking gate. Additionally, because of the mechanical nature of the conductor, variations in performance are inherent in the conductor due to material wearing and aging. Furthermore, the flat braided flexible wire is not able to provide the user of the monitor with an easily concealable device.

An orthopedic weight monitor relying on a multi-layered assembly is taught in '930. An insole having three overlaying sheets of a plastic material bonded together is disclosed. The intermediate sheet has cut-outs of the heel, toe and ball portions of the sole to create three separate internal chambers. A plurality of fingers formed of conductive ink forms a mechanical switch. The conductive ink is disposed on the outer layers of plastic and contact each other as force is applied to the assembly to signal pressure is being applied to the patient's foot. As a result of the close proximity of the layers of plastic material, the performance of the switches is subject to variations resulting from wear of the plastic layering material and the shoe that is used as a carrier for the assembly. Additionally, as a patient heels there are no provisions for varying the amount of pressure required to cause a signal. An entire new monitor must be adapted to the patient to vary the amount of pressure required to produce a signal.

Furthermore, '918 discloses a plurality of transducers for measuring the pressure at a number of points as a function of time. Each of the transducers is connected to a microprocessor. The device is particularly adapted to the problem of diabetics who experience low blood pressure levels over a period of time. The device uses a number of transducers located throughout a foot pad. The device is a multi-event notification system for informing a user when any number of sensing points reaches a preselected threshold of pressure over a time interval. There is no provision for, or teaching of, a device to warn the user of an excessive instantaneous application of pressure. The devise is designed to monitor a large number of pressure points. Therefore, the device is not suitable for economical application because of the complexity of the device.

In an article in *Medical & Biological Engineering & Computing*, Sept. 1978, an article titled "Limb-Load Alarm Device for Partial-Weight-Bearing Walking Exercise" a device was disclosed for measuring the limb load with two removable load transducers attached to the sole of a patients shoe. The transducers are constructed of a rectangular plate supported by a plurality of neoprene rubber sponges. Each sponge has a vinyl chloride sheet adhered to a lower wear surface of the sponge. The transducer relies on the plate flexing between the supporting sponges to determine the amount of loading the user is subjecting a limb. The article does not teach, nor suggest, the applicant's invention that uses a flexible pad material to continuously supported a plate for determining the amount of lower extremity loading. Furthermore, the transducer described in the article is 7 millimeters thick and thereby curtails use in a shoe sole. The thickness of the transducers interferes with the normal gate of a patient that is fitted with the transducer. There is no teaching of the transducer used in the Applicant's invention which is easily inserted into the shoe of the user and does not interfere with a patient's normal gait.

A flexible force sensor having an electrical conductor releasably attached to a test site is disclosed in U.S. Pat. No. 4,426,884 to Polchaninoff. The sensor has a plurality of relatively spaced hemispherical electrical contacts and conductors supported such that when a force is applied to the sensor, electrical resistance is produced as a function of the applied force. The disclosure relies on an induced change in electrical resistance to measure forces. The sensor comprises an electrode platform and flexible conductive sensor. The disclosure teaches a platform and sensor that are releasable attached to a test site for the determination of forced applied to the test site. Because the sensor is releasably attached to test site, there is no teaching of an orthopedic monitor that is easily positioned by a layman or impaired patient. Furthermore, the flexible and dynamic nature of the patient's foot during walking inhibits proper attachment of a sensor directly to the patient's foot. Additionally, the mechanical nature of the sensor makes the disclosure susceptible to failures resulting from excessive pressure and repeated flexing.

Other methods of warning a patient when a predetermined load has been reached in a lower extremity are illustrated in U.S. Pat. Nos. 3,791,375 to Pfeiffer and U.S. Pat. No. 3,974,491 to Sipe. Fluid containing load cells are disclosed in '375. The load cells are located below the ball and heel of a patient's foot. As pressure is applied to the cells, fluid is forced from the chamber as a function of the load applied by the patient's foot. The disclosure teaches a bellows connected to the cells via tubes to measure the flow out of and into the cell for determining the amount of load a lower extremity is subjected. Additionally, a single resilient liquid filled tube within a resilient foot pad adapted to fit inside a shoe is disclosed in '491. The monitoring device is controlled by pressure resulting from compression on the flexible tubing. Both disclosures '375 and '491 are susceptible to failure from punctures to the fluid bladders. Furthermore, the mechanical nature of fluid transfer within a tube and the size of the tubing required to transfer load information to a monitoring device precludes easy concealment or remote location of the tubing and sensing devices.

Finally, U.S. Pat. No. 3,658,052 to Alter discloses a device for the detection of movement by attaching a magnet to an object to be monitored. The disclosure teaches a pickup coil located such that movement by the object having the magnet attached to it induces a voltage in the coil. The output from the coil is delivered to a circuit where pulses are generated for signalling an alarm. The disclosure makes no provision for portability since the motion of an object can only be detected by a stationary coil. Furthermore, there are no provisions for determining any information other than movement relative to the coil. There is no teaching to monitor the amount of pressure applied to a lower extremity for orthopedic purposes.

As illustrated by the background art, efforts are continuously being made in an attempt to improve orthopedic weight monitors. No prior effort, however, provides the benefits attendant with the present invention. Additionally, the prior patents and commercial techniques do not suggest the present inventive combination of component elements arranged and configured as disclosed and claimed herein.

The present invention achieves its intended purposes, objects, and advantages through a new, useful and unobvious combination of method steps and component elements, with the use of a minimum number of functioning parts, at a reasonable cost to manufacture, and by employing only readily available materials.

Therefore, it is an object of this invention to provide an improved orthopedic weight monitor for detecting weight bearing on a lower extremity for medical purposes, comprising in combination: a flexible pad having a thickness of between about $\frac{1}{8}$ and $\frac{1}{4}$ inches shaped for conforming to the bottom of a human foot for placement inside of a shoe or incorporated into a cast or splint, the pad having a heel portion and a toe portion, the heel portion located cooperable with the heel of a user; a sensor encased within the heel portion of the pad to be located beneath the heel of the user, the sensor comprising a thin, rigid rectangular plate and a foil strain gage coupled therebeneath, the plate having two opposing exterior edges which are turned inwardly to form support peripheral edges; an electronic module remotely positioned from the sensor and removably coupled to the body of the user for receiving signals from the foil sensor, wherein the electronic module signals the user to a prescribed level of weight bearing by at least one of the following methods: vibration, sound, light, continual analog and digital; and electrical lines extending to exterior of the pad between the sensor and the receiver, the electrical lines being removably coupled to both the sensor and electronic module.

Another object of the invention is to detect the amount of weight bearing on a patients foot to monitor the effect upon a lower extremity prosthesis, fractures of the lower extremity, bone grafting, soft tissue pathology during the healing process of the patient which is healing and/or other conditions in a safe, secure, convenient and economical manner.

A further object of this invention is to provide a rapid, reliable method of notifying a patient when a prescribed weight load limit on the worked limb has been reached for proper rehabilitation.

A further object of this invention is to readily indicate to a patient unadvised weight bearing despite the loss of most other senses by the patient.

A further object of this invention is to adjust the initiate point of a signal to the patient depending on the individual weight bearing situation of the particular patient at that time.

A further object of this invention is to allow for a physician and/or patient to calibrate and recalibrate a weight detecting monitor to retain accuracy.

A further object of this invention is to record, alert and/or educate a patient to levels of weight bearing by vibration, sound, light, continual analog readout or digital readout.

A further object of this invention is a variant ability to produce a record of the patient's activities to indicate the time and duration of pressures which comply or exceed that recommended by the physician.

A further object of this invention is to add or delete from a weight monitor in order to adjust the sophistication of the alerting and recording functions to address the changing physical needs and/or economic strictures of an individual patient.

A further object of this invention is to monitor a patient who requires life term monitoring of weight bearing.

A further object of this invention is to weight monitor a patient's normal environment providing a notification signal presented as sound, light or vibration, whichever is most suitable to the patient's environment.

A further object of this invention is to generate in a rehabilitation center environment a signal that can be monitored remotely by a therapist for aiding in patient progress analysis.

A further object of this invention is to provide, where medically indicated, a monitor that can be modified to provide two signals, a first for acceptable loading and a second for overloading.

A further object of this invention is to monitor and record for medical and/or insurance reasons, a monitor to record each load bearing to indicate over-use/overloading or inactivity and under-loading.

The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into a shoe having a sole and an upper coupled adjacent to their peripheries defining a foot-receiving space therebetween and an opening for passage of a wearer's foot; a flexible pad means shaped for conforming to the bottom of a foot positioned inside the space for receiving a wearer's foot thereon, the pad having a heel portion positionable beneath the heel of a wearer; sensor means encased within the heel portion of the pad means to be located beneath the heel of the wearer, the sensor means comprising a thin, rigid rectangular plate means having a foil strain gage means coupled therebeneath; electronic module means remotely positioned from the sensor means to receive signals from the foil sensor means; and electrical line means between the flexible pad means and the electronic module means.

The invention may also be incorporated into an improved orthopedic weight monitor for detecting weight bearing on a lower extremity for medical purposes, comprising in combination flexible pad means shaped for conforming to the bottom of a foot for placement inside of a shoe, the pad having a heel portion positionable beneath the heel of a user; sensor means encased within the heel portion of the pad means to be located beneath the heel of the user, the sensor means comprising a thin, rigid rectangular plate means having a foil strain gage means coupled therebeneath; electronic module means remotely positioned from the sensor means to receive signals from the foil sensor means; and electrical line means between the flexible pad means and the electronic module means.

The two opposing edges of the plate means include an exterior edge which is turned inwardly to form two supporting peripheral edges. The plate means is constructed of 26 gage stainless steel. The pad means is of a thickness between about $\frac{1}{8}$ inches and $\frac{1}{4}$ inches. The electronic module means is removably coupled on the clothing of the user. The electronic module means is removably coupled on the body of the user. The electronic module means signals the user to a prescribed level of weight bearing by vibrational means. The electronic module means signals the user to a prescribed level of weight bearing by audible means. The electronic module means signals the user to a prescribed level of weight bearing by luminous means. The electronic module means signals the user to a prescribed level of weight bearing by continuous analog display means. The electronic module means signals the user to a prescribed level of weight bearing by digital display means. The improved orthopedic weight monitor further includes means in the electronic module to adjust to detect and record varying levels of weight bearing on the lower extremity by the user. The electrical line means extending exterior of the pad means are removably coupled to the sensor means exterior of the pad means. The sensor means and electronic module means are coupled by radio frequency means. The sensor means and electronic module means are coupled by infra red light means. The sensor means is incorporated in a cast. The sensor means is incorporated in a splint.

The invention may also be incorporated into an improved orthopedic weight monitor for detecting weight bearing on a lower extremity for medical purposes, comprising in combination flexible pad means having a thickness of between about $\frac{1}{8}$ and $\frac{1}{4}$ inches shaped for conforming to the bottom of a foot for placement inside of a shoe, the pad having a heel portion and a toe portion, the heel portion located cooperable with the heel of a user; sensor means encased within the heel portion of the pad means to be located beneath the heel of the user, the sensor means comprising a thin, rigid rectangular stainless steel plate means and a foil strain gage means coupled therebeneath, the plate means having a thickness of about 0.020 inches plus or minus 10% and two opposing exterior edges which are turned inwardly to form two support peripheral edges; electronic module means remotely positioned from the sensor means and removably coupled to the body of the user for receiving signals from the foil sensor means, wherein the electronic module means signals the user to a prescribed level of weight bearing by at least one of the following methods: vibration, sound, light, continual analog and digital; and electrical line means extending to exterior of the pad means between the sensor means and the electronic module means, the electrical line means being removably coupled to both the sensor means and electronic module means. The pad means is incorporated in a cast. The pad means is incorporated in a splint.

Lastly, the invention may be incorporated into a method of providing improved orthopedic weight monitoring for the detection of weight bearing on a lower extremity for medical purposes, comprising, in combination, the steps of providing a flexible pad means shaped for conforming to the bottom of a foot for placement inside of a shoe, the pad having a heel portion and a toe portion positionable beneath the heel of a user; monitoring sensor means encased within the heel portion of the pad means to be located beneath the heel of the user, the sensor means comprising a thin, rigid rectangular plate means having a foil strain gage means coupled therebeneath; providing electronic module means remotely positioned from the sensor means to receive signals from the foil sensor means; and furnishing electrical line means extending to exterior of the flexible pad means between the foil stain gage means and the electronic module means.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention as set forth in the appended claims.

BRIEF DESCRIPTION OF THE DRAWINGS

For a fuller understanding of the nature and objects of the present invention, reference should be had to the following detailed description taken in conjunction with the accompanying drawings in which:

FIG. 1 is a perspective view of the primary embodiment of the invention.

FIGS. 1A, 1B and 1C show alternate forms of an electronic module.

Similar reference characters refer to similar parts throughout the several FIGS.

DETAILED DESCRIPTION OF THE INVENTION

Shown in FIGS. 1 through 5 are various views of the primary embodiment of the improved orthopedic weight monitor constructed in accordance with the principles of the preferred embodiment of the present invention.

From an overview standpoint, the improved orthopedic weight monitor 10 is adapted for use with a human patient with a lower extremity condition that necessitates restricted weight bearing. Patients, who for one of many of medical reasons, are instructed by their attending physician not to apply more than a particular weight to the extremity to make optimal conditions for proper healing. See FIG. 1.

Figure 8:
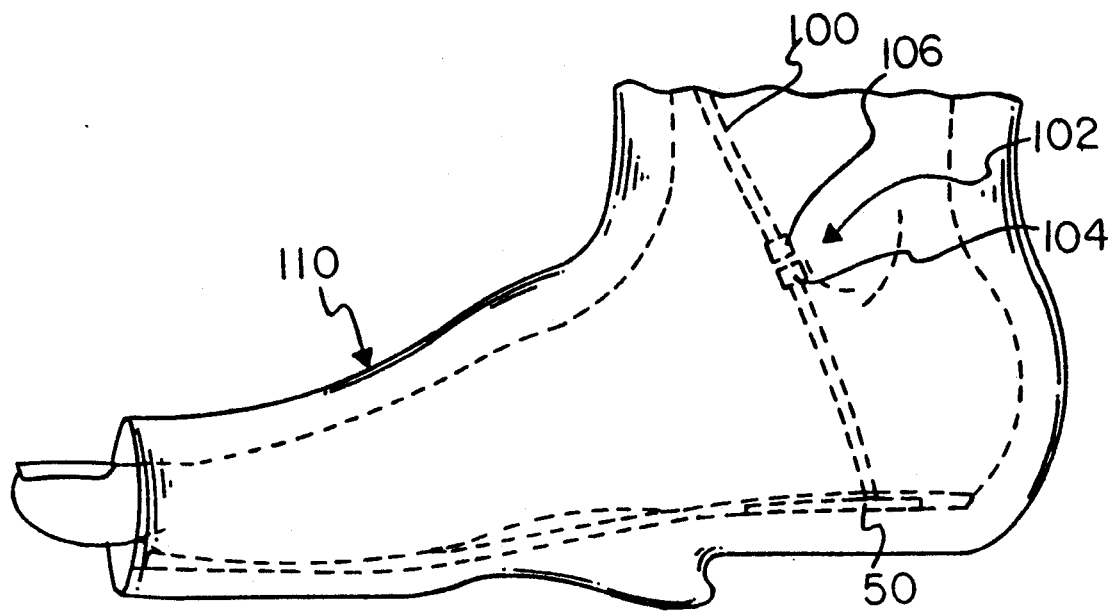
FIG. 8 is a sectional view of an alternate embodiment of the invention.
Figure 9:
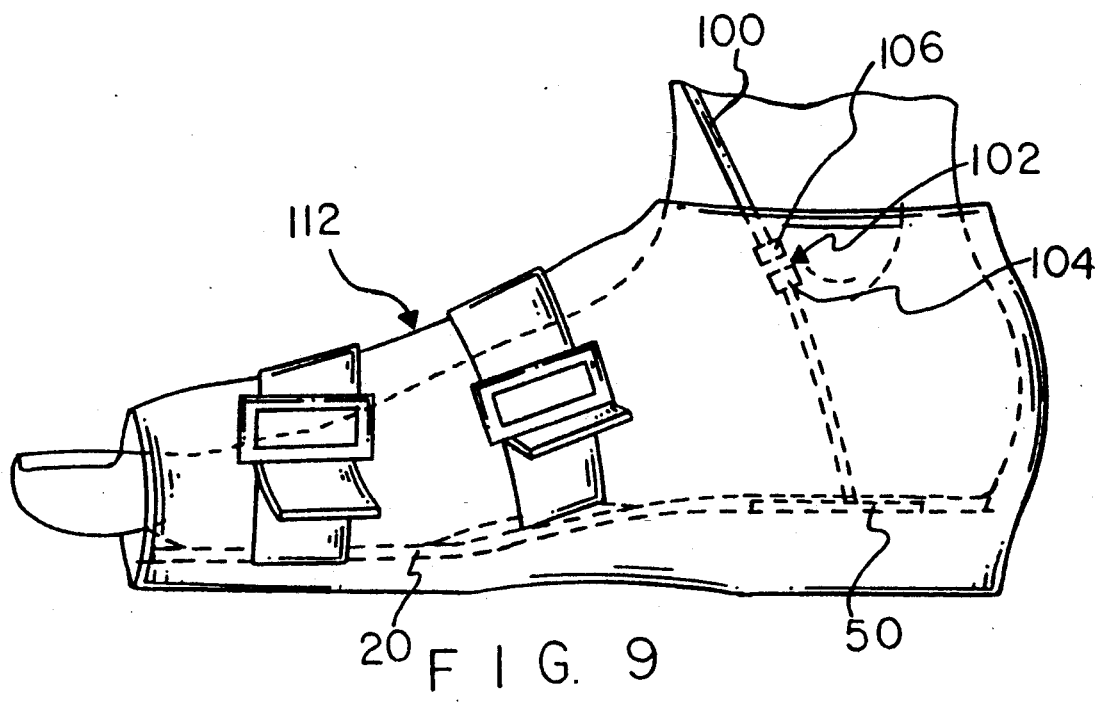
FIG. 9 is a sectional view of an alternate embodiment of the invention.

The monitor 10 includes a flexible pad 20 shaped for conforming to the inside of a shoe or slipper 12. See FIG. 2. Alternately, the monitor may be incorporated into a walking cast 110 or splint 112. See FIGS. 8 and 9. In the primary embodiment as shown in FIGS. 1 through 4, the pad 20 has a heel portion 22 and a toe portion 24. Alternately, the pad may have only a heel portion 22. In the preferred embodiment, the pad is of a thickness between about ⅛ inches and ¼ inches plus or minus about 10%. Preferably, the pad 20 is constructed of a flexible, closed-cell material which is impervious to moisture, preferably latex. The shape, material and thickness of the pad 20 allows the monitor 10 to be easily placed within the shoe 12 of a user or incorporated into a cast 110 or splint 112. The heel portion 22 of the pad is positionable beneath the heel 26 of a user of the monitor 10. The positioning of the heel 26 portion of the pad allows the user's heel to fully contact the monitor. The placement of the monitor 10 beneath a patient's foot allows the doctor to detect and monitor the amount of weight bearing on a patient's entire lower extremity. Due to the pad's 20 thin profile, the monitor does not interfere with the normal walking gait of the patient. Alternately, the pad 20 may be incorporated in a cast 110 or splint 112 and still not interfere with the patient's normal walking gait. This arrangement allows the patient to walk with a normal as possible gait, keeping in mind their weight bearing restrictions and injury.

The monitor 10 further includes a sensor 50 encased within the heel portion 22 of the pad. See FIGS. 3 and 4. The sensor is located beneath the heel 26 of a user. Due to the location of the sensor, as the user applies pressure to his foot, the heel applies pressure to the sensor 50. The sensor allows the doctor to determine the amount of weight being applied by the foot and thereby bearing upon the entire lower extremity or other area that is healing. The sensor comprises a thin, rigid rectangular plate 52 having a foil strain gage 54 coupled therebeneath. Furthermore, in the preferred embodiment, the plate 52 is constructed of stainless steel, a thickness of about 0.020 inches plus or minus 10%, in a square about 2 inches by 2 inches plus or minus about 10% or a similar substitute therefor. Additionally, two edges 56 of the plate 52 include two opposing exterior edges 58 which are turned inwardly to form two supporting peripheral edges 60. The edges 60 are axially aligned in the direction of movement of the monitor. However, the edges 60 can be oriented in any direction without diminishing the monitor's performance. These edges 60 provide a support bearing points for the plate. The edges 60 insures the accuracy of the stain gage 54. In other words, the two edges of the plate are turned under or hemmed to provide bearing points for the plate. The sensor in the preferred form is a foil stain gage 54 which is affixed to the bottom 62 of the plate 52 between the bearing points 60.

The plate 52 and strain gage 54 are completely embedded within the flexible pad 20 of the monitor 10. Therefore, the plate 52 is continuously and uniformly supported by the pad in which it is encased. The plate 52 is in intimate and reproducible contact with the patient's foot 26. Thus, as the plate 52 deflects, the length of the stain gage 54 is changed, thereby changing the flow of current through the gage 54. The change in current flow in the stain gage is used to determine weight bearing in increments up to full function weight bearing. An added benefit of the plate 52 and stain gage 54 being completely embedded within the flexible pad 20 is that the plate and gage are protected from damage and exposure by the pad material, as well as adding to the patient's comfort and hygiene.

Essentially, the plate acts 52 as a simple beam. See FIG. 4. A loading situation created by a center loading of a plate which is supported at both ends 60. The plate loading creates deflection. The foil strain gage 54 is coupled to the bottom 62 of the plate 52. The foil stain gage 54 is a section of an electrical circuit. Deflection changes the length of the foil strain gage and thereby alters electrical resistance within the strain gage.

In other words, the utilization of the strain gage 54 in the present invention when coupled to a flexible plate 52 with inturned edges 60 functions in a manner analogous to a beam supported at its opposite ends. The inturned edges 60 of the present invention are analogous to the end supports in that they tend to restrict movement and deformation. The central portion of the plate between the inturned edges 60 is analogous to the beam supported by the end supports. When weight is placed on the beam between the end supports whether locally or distributed across its length, the beam will deflect downwardly normally with the greatest deformation at its center. By analogy when weight is placed on the plate 52 of the present invention through the application of a patients weight, it too will deform centrally between the inturned edges with its greatest deformation at the center thereof. The deformation of the plate 52 effects a deformation of the strain gage 54. It is the deformation of the strain gage 54 which determines the reading of the instrument 10. By analogy, the deformation of the beam can be used to calculate the weight applied to the beam between the end supports.

The presence of the pad material 20 changes the simplicity of the plate 52. The durometer of the pad material 20 creates a resistance to the deflection of the plate 52.

An electronic module 80 is remotely positioned from the sensor for receiving signals from the foil gage 52. In the primary embodiment, the electronic module 80 has a switch 82 for turning the electronic module on and off. Additionally, the electronic module may have a calibrator 84 for varying the initiation point of a signal depending on the situation of the particular patient. This also allows for periodic recalibration of the device to retain accuracy of measurements. In other words, if initially the doctor prescribes no weight be applied to the lower extremities, the monitor 10 can be programmed accordingly. If the doctor allows 20 pounds or 40 pounds or some other specific weight, adjustment of the electronic module 80 could also be made appropriately. Additionally, the electronic module can be set to detect or record varying levels of weight bearing on the lower extremity by the patient. The strain gage 54 is part of a wheatstone bridge. The bridge is an electrical circuit arrangement that transposes a variation in resistance to a variable output. The output can be used in a variety ways depending on the electronic module attached to it.

The electronic module 80 functions to alert the patient or doctor of a prescribed level of weight bearing by a signal 86. In the primary embodiment, the signal is a sound. Alternately, the signal may consist of a vibration, luminary, etc. or other continuous analog or digital display 80. The type of signal most appropriate for the patient or doctor may be chosen or a multitude of signals may be utilized. For example, for patients having a hearing impairment the electronic module 80 may emit a vibrational signal. Alternately, the electronic module may emit a luminary signal 86 to enable an attending doctor to observe a patient walking, thereby allowing the doctor to determine when a prescribed loading of an extremity is exceeded.

Finally, in the primary embodiment, the electronic module 80 is removably coupled to the clothing of a patient. See FIG. 1. A fastener 92 removably couples the module 80 and patient's clothing. The fasteners 92 may be a clip type fastener or a hook type fastener. Alternately, the electronic module could be removably coupled to the body of a patient by a strap and buckle type fastener. Placement of the module 80 on the patient's belt allows easy interaction between the patient and module. Flexibility of electronic module placement facilitates any special needs of the patient. If the patient lacked upper body mobility, the electronic module could be placed accordingly. As needed, the patient could removably couple the monitor 80 to a belt, shirt, pocket, or shoe. Alternately, the module could be removably coupled to the body of a patient by a strap and buckle type fastener, thereby allowing the module to be removably coupled to the patient during bathing, therapy or if normal clothing is not being worn by the patient.

In the primary embodiment, electrical lines 100 extend from exterior of the flexible pad 20 between the foil stain gage 52 and the electronic module 80. A pair of electrical lines 100 or a coaxial electrical line 100 may be used between the foil strain gage 52 and the electronic module 80. The electrical lines allow the electronic module to be placed remotely from the sensor 50. The wires are easily concealable within the clothing of the patient for providing an unobtrusive monitoring device 10.

The electrical lines 100 are preferably removably coupled to the sensor 50 and electronic module 80. The electrical 102 couplers are exterior of the pad 20 and exterior of the electronic module 80. Each electrical line coupler 102 comprises a co-operable female 104 and male portion 106. By way of example, modular telephone type jacks or ribbon cable type connectors can be used to removably couple the sensor 50 and module 80. The couplers 102 allow either the sensor 50 or electronic module 80 to be replaced independently of each other in case of failure of either part. The couplers 102 also allow the electronic module 80 to be removed from the patient for adjustments or data recovery without disturbing the sensor 50 attached to the patient. Furthermore, the couplers 102 facilitate installing the monitor 10 on the patient by allowing the electronic module 80 and sensor 50 to fitted to a patient independently of each other. Thereafter, the wires 100 can be concealed within the patient's clothing.

Figure 10:
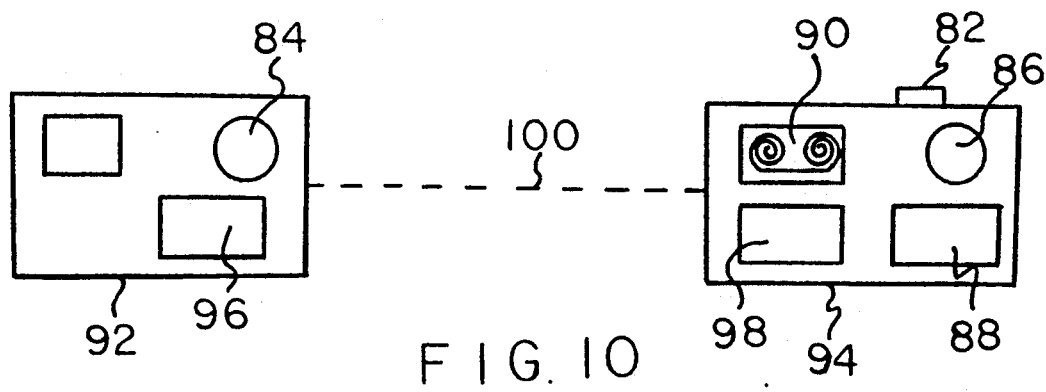
FIG. 10 is a schematic showing the primary and secondary electronic module of an alternate embodiment.

In an alternate embodiment, the electronic module 80 comprises a primary module 92 and secondary module 94. See FIG. 10. Electrical lines 100 extend from exterior of the flexible pad 20 between the foil strain gage 54 and the primary electronic module 92. The electrical lines 100 are preferably removably coupled to the module primary electronic module 92 and secondary electronic module. The primary module may contain a calibrator 84 for varying the initiation point of a signal 86 depending on the situation of the particular patient. Additionally, the primary module 92 contains a transmitter 96. The transmitter 96 sends radio frequencies to the secondary module 94 for coupling the primary 92 and secondary modules 94. Alternately, the transmitter 96 could send infra-red light to the secondary module 94 for coupling the primary 92 and secondary modules 94.

In a further alternate embodiment, a more elaborate electronic module 80 can record the patient's activity to indicate the time and duration of pressures which exceed that recommended by a doctor. The monitor 10 would create the record 90 on tape, micro chip or E. prom. The record 90 of the patient's activity would allow the doctor to have an accurate record of the patient's activities. The record 90 would enable the doctor to access whether proper adherence to medical instruction is being followed by the patient. Alternately, by analyzing the record of time and duration of pressures a patient put on a lower extremity, a doctor would be able to verify a suspect injury to the patient's lower extremity or analysis if a potential injury was acquired during the healing process. Furthermore, recording ability of the module 80 can be incorporated into the primary embodiment of the present invention.

The secondary electronic module 94 contains a receiver 98 for receiving radio frequencies sent by the primary module 92. Alternately, the receiver 98 in the secondary module 94 could be capable of receiving infra-red light send by the primary module 92. Furthermore the secondary module contains a switch 82 for turning the module on and off. The module 94 alerts a patient or doctor of a prescribed level of weight bearing by a signal 86. The signal is usually a sound, but the signal may be a vibration, luminary, etc. Additionally, the module 94 may contain a continuous analog or digital display 88. Finally, the electronic module 94 could record time an duration of pressures that were transmitted to the secondary module 94 from the primary module 92. By way of example, the record 90 could be in the form of a cassette tape, micro chip or E prom. Furthermore, the features of the alternate embodiment may be incorporated into the primary embodiment of the present invention.

During activity of a patient, or when other circumstances dictate, connection of the primary electronic module 92 and the secondary electronic module 94 by radio frequencies or infra-red light would enable remote monitoring of a patient without necessitating a long electrical line 100 between the electronic module 94 and the sensor 50. There would no longer be a need for concealment of the monitor's electrical lines 100, nor would there be any electrical lines 100 to fail or get entangled with obstructions.

In the operation and use of the apparatus of the present invention 10, there is provided a method of improved orthopedic weight monitoring. The above descriptions relate to an apparatus 10 for detecting weight bearing on a patient's entire lower extremity, using a monitor 10 placed in contact with a patient's foot 26. Patients who have any kind of orthopedic condition that restricts the weight bearing capabilities of their lower extremities involving the foot, leg, hip or pelvis that necessitates restricted weight bearing are instructed by their attending physician not to apply more than a particular weight to the extremity to facilitate proper healing of the condition. The method comprises a number of steps in combination.

First, the method includes the step of providing a flexible pad 20 shaped for conforming to the bottom of a foot for placement inside of a shoe 12 as described above. The next step of placing the monitor 10 in a patient's shoe 12 or incorporating the monitor in a cast 110 or splint 112 allows the doctor to detect and monitor the amount of weight bearing on a patient's lower extremity. The pad's 20 thin profile does not interfere with the normal walking gait of the patient. Therefore, the patient is not forced to learn any new walking skills when fitted with the monitor 10.

Thereafter, the method monitors a sensor 50 as described above. As a patient arises, stands, walks, sits or otherwise applies pressure to his foot, the heel 26 applies pressure to the plate 52. The plate's 52 deflection changes the length of the stain gage 54. The change in length of the stain gage 52 varies the amount of current flowing through the gage 52, thereby measuring weight bearing in increments up to full function weight bearing. The sensor 50 measures the amount of weight being applied by the user's foot 26 and thereby bearing upon the entire lower extremity and pelvis.

Figure 2:
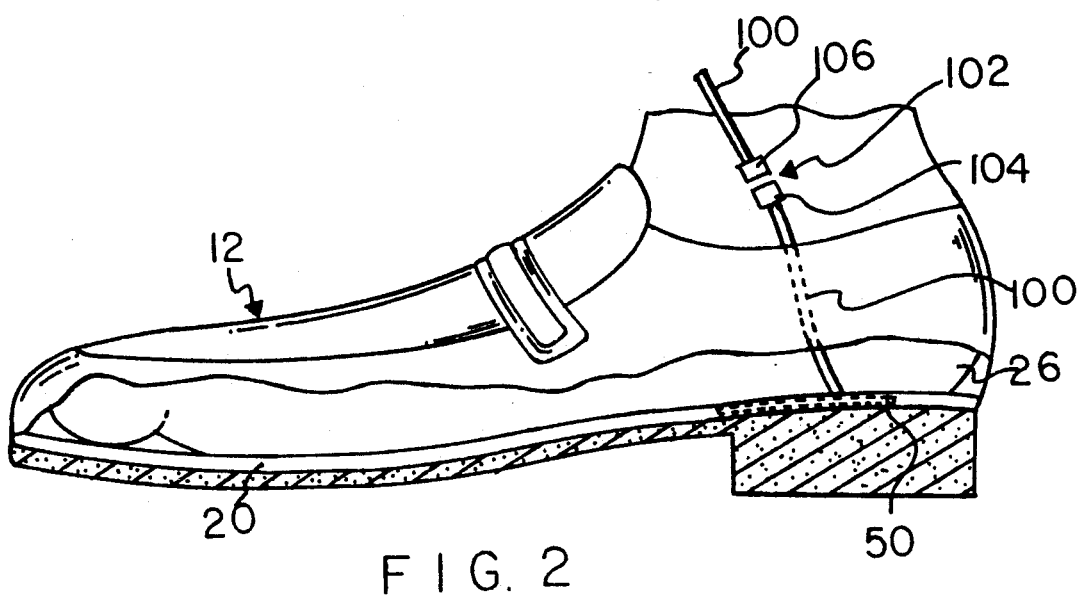
FIG. 2 is a longitudinal section of the flexible pad and sensor.
Figure 3:
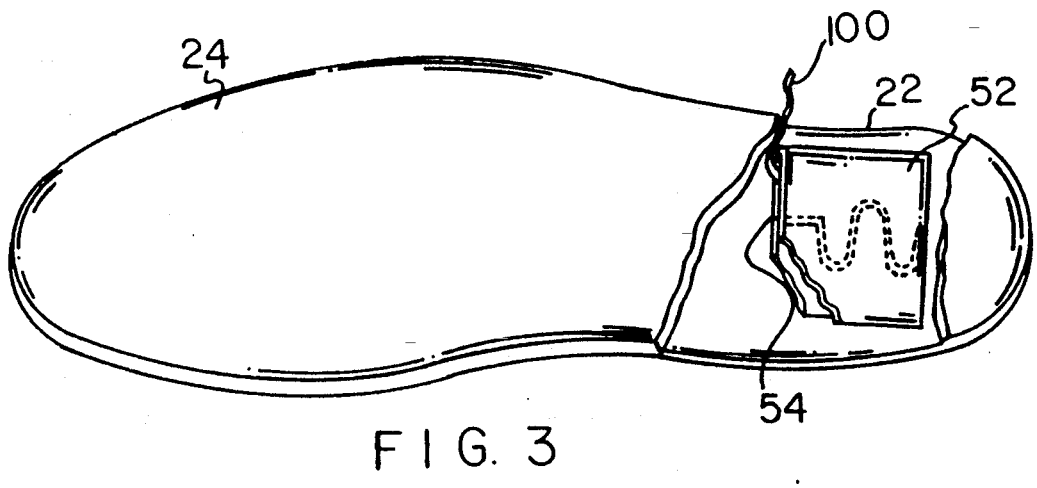
FIGS. 3 is a horizontal section of the flexible pad of the primary embodiment showing the sensor.
Figure 4:
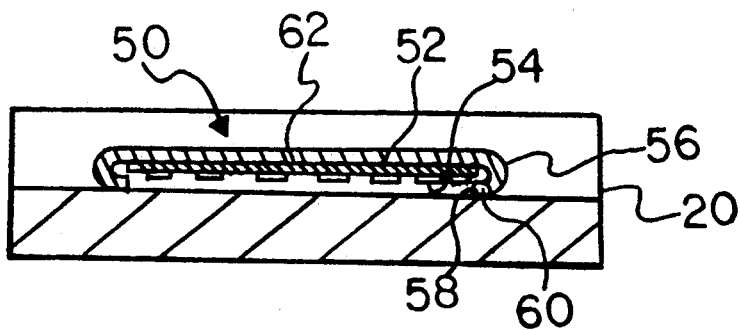
FIG. 4 is a cross-section through the flexible pad showing the sensor.
Figure 5:
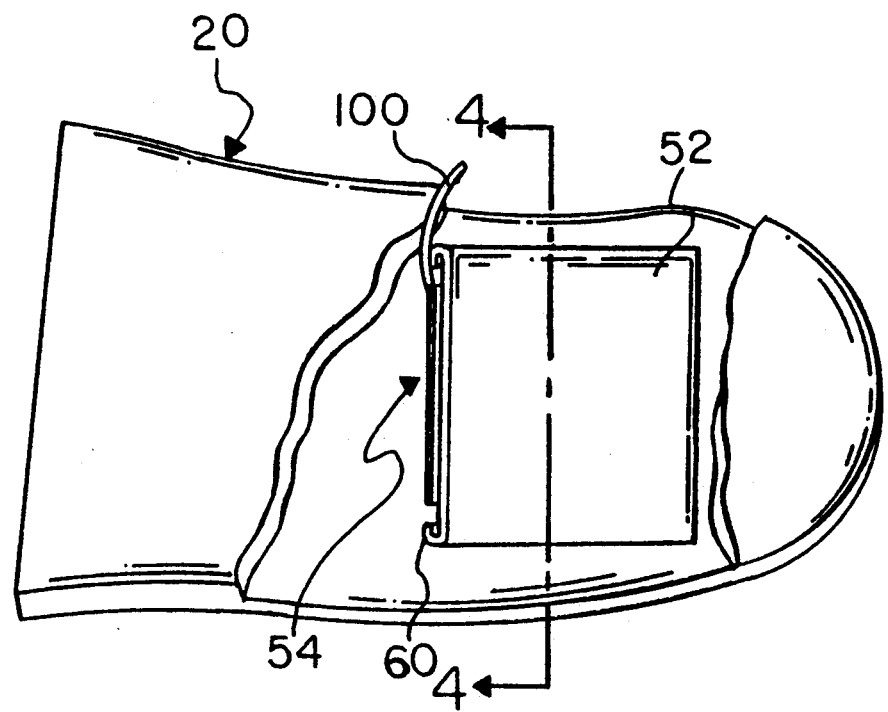
FIG. 5 is a perspective view of an alternate embodiment of the invention.
Figure 6:
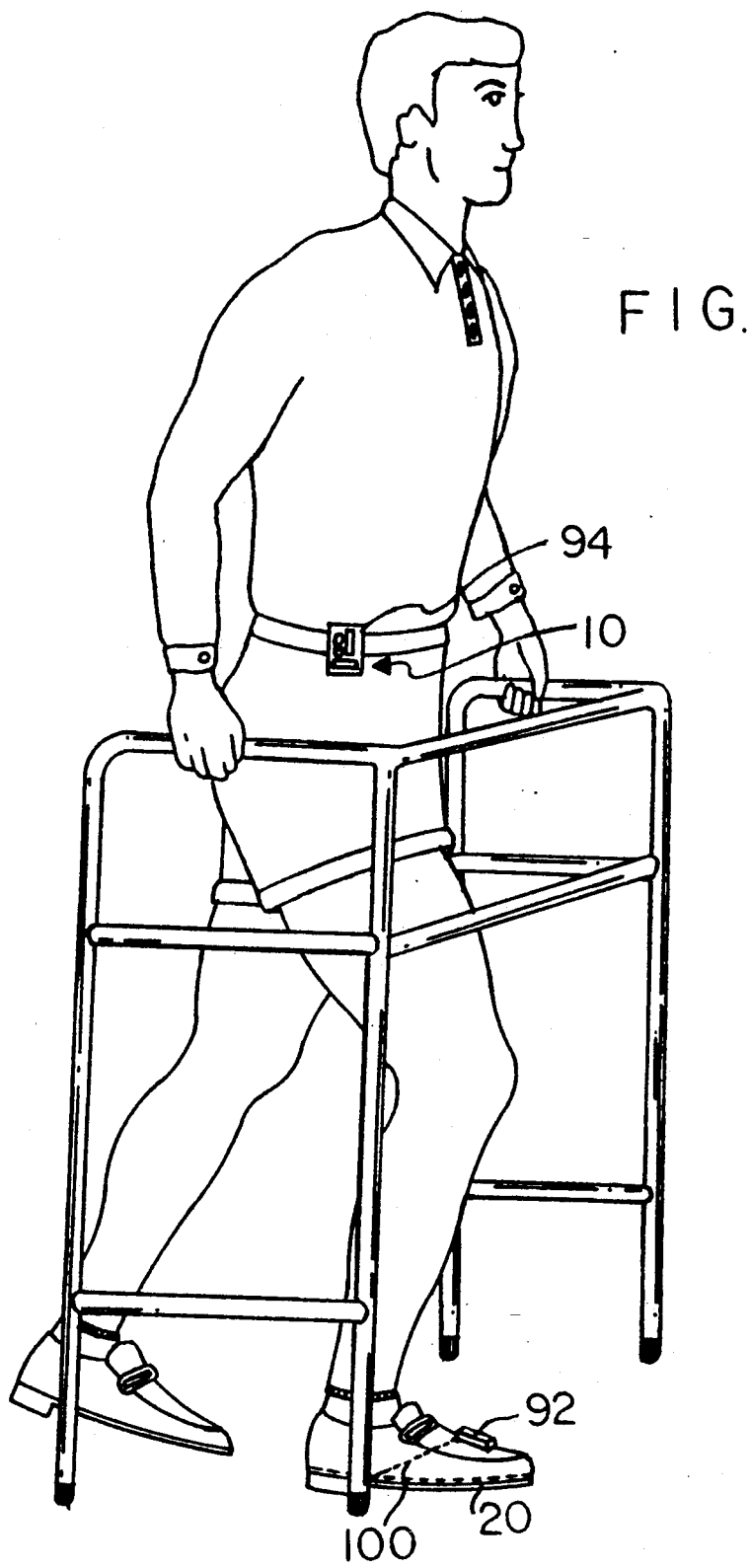
FIG. 6 is a perspective view of an alternate embodiment of the system.
Figure 7:
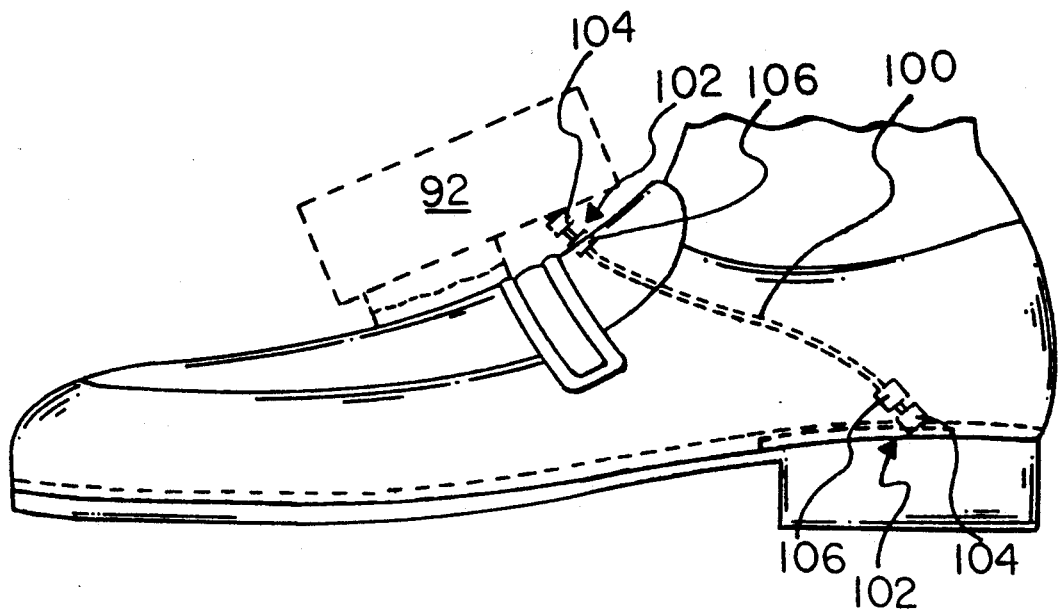
FIG. 7 is a side view of an alternate embodiment of the invention.

Subsequently, the method provides a electronic module 80 as described above. The electronic module 80 is adjustable to vary the initiation point of a signal 86 depending on the situation of the particular patient. Additionally, the electronic module 80 can be adjusted to detect or record varying levels of weight bearing on the lower extremity by the patient. The electronic module 80 functions to alert the patient or doctor of a prescribed level of weight bearing by a signal 86. The signal consists of preferably an audible tone. Alternate embodiments include luminary, vibration, etc. and other continuous analog display or digital display as described above. The type of signal 86 most appropriate for the patient or doctor may be chosen or a multitude of signals may be utilized. Additionally, the electronic module 80 records the patient's activity to indicate the time and duration of pressures which exceed that recommended by a physician. The record would enable the physician to access whether compliance with a recommended weight bearing regime is being adhered to by the patient. Subsequently, the electronic module 80 is removably coupled to the clothing or body of a patient. For example, if the patient lacked upper body mobility, the electronic module 80 could be placed accordingly. As needed, the patient could removably couple the monitor to a belt, shirt, pocket, or shoe. Coupling of the monitor to the shoe is shown in FIGS. 6 and 7. Alternately, the monitor 10 can be removably coupled to the patient during bathing or therapy.

Lastly, the method furnishes electrical lines 100 as described above. The electrical lines 100 allow the electronic module 80 to be placed remotely from the sensor 50. The wires 100 are easily concealable within the clothing of the patient for providing an unobtrusive monitoring device 10. The couplers 102 allow either the sensor 50 or electronic module 80 to be replaced independently of each other in case of failure of either part. The couplers 102 also allow the electronic module 80 to be removed from the patient for adjustments or data recovery without disturbing the sensor 50 attached to the patient. Furthermore, the couplers facilitate installing the monitor 10 on the patient by allowing the electronic module 80 and sensor 50 to fitted to a patient independently of each other. Thereafter, the wires 100 can be concealed within the patient's clothing.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

Now that the invention has been described,
What is claimed is:

1. A shoe having a sole and an upper coupled adjacent to their peripheries defining a foot-receiving space therebetween and an opening for passage of a wearer's foot; a flexible pad means shaped for conforming to the bottom of a foot positioned inside the space for receiving a wearer's foot thereon, the pad means having a heel portion positionable beneath the heel of a wearer; sensor means encased within the heel portion of the pad means to be located beneath the heel of the wearer, the sensor means comprising a thin, rigid rectangular plate means and a foil strain gage means coupled therebeneath, the plate means having means at opposed edges to minimize deflection of the plate means about an axis extending from one opposed edge to the other; electronic module means remotely positioned from the sensor means to receive signals from the foil stain gage means; and electrical line means between the sensor means and the electronic module means.

2. An improved orthopedic weight monitor for detecting weight bearing on a lower extremity for medical purposes, comprising in combination:
flexible pad means shaped for conforming to the bottom of a foot for placement inside of a shoe, the pad means having a heel portion positionable beneath the heel of a user;
sensor means encased within the heel portion of the pad means to be located beneath the heel of the user, the sensor means comprising a thin, rigid rectangular plate means, the plate means having opposed edges which minimize deflection of the plate means about an axis extending from one opposed edge to the other and a foil strain gage means coupled therebeneath;
electronic module means remotely positioned from the sensor means to receive signals form the foil strain gage means; and
communication means between the sensor means and the electronic module means.

3. The improved orthopedic weight monitor set forth in claim 2, wherein two opposed edges of the plate means include an exterior edge which is turned inwardly to form two supporting peripheral edges.

4. The improved orthopedic weight monitor set forth in claim 2, wherein the plate means is constructed of 26 gage stainless steel.

5. The improved orthopedic weight monitor set forth in claim 2, wherein the pad means is of a thickness between about $\frac{1}{8}$ inches and $\frac{1}{4}$ inches.

6. The improved orthopedic weight monitor set forth in claim 2, wherein the electronic module means is adapted to be removably coupled on the clothing of the user.

7. The improved orthopedic weight monitor set forth in claim 2, wherein the electronic module means is adapted to be removably coupled on the body of the user.

8. The improved orthopedic weight monitor set forth in claim 2, wherein the electronic module means includes vibrational means to signal the user to a prescribed level of weight bearing.

9. The improved orthopedic weight monitor set forth in claim 2, wherein the electronic module means includes audible means to signal the user to a prescribed level of weight bearing.

10. The improved orthopedic weight monitor set forth in claim 2, wherein the electronic module means includes luminous means to signal the user to a prescribed level of weight bearing.

11. The improved orthopedic weight monitor set forth in claim 2, wherein the electronic module means includes continuous analog display means to signal the user to a prescribed level of weight bearing.

12. The improved orthopedic weight monitor set forth in claim 2, wherein the electronic module means includes continuous digital display means to signal the user to a prescribed level of weight bearing.

13. The improved orthopedic weight monitor set forth in claim 2, further including means in the electronic module to adjust, to detect and to record varying levels of weight bearing on the lower extremity by the user.

14. The improved orthopedic weight monitor set forth in claim 2, wherein communication means extending exterior of the pad means are removably coupled to the sensor means exterior of the pad means.

15. The improved orthopedic weight monitor set forth in claim 2, wherein the communication mans is radio frequency means coupling the sensor means and electronic module means.

16. The improved orthopedic weight monitor set forth in claim 2, wherein the communication means is infra red light means coupling the sensor means and electronic module means.

17. The improved orthopedic weight monitor set forth in claim 2, wherein the sensor means is incorporated in a cast.

18. The improved orthopedic weight monitor set forth in claim 2, wherein the sensor means is incorporated in a splint.

19. An improved orthopedic weight monitor for detecting weight bearing on a lower extremity for medical purposes, comprising in combination:
flexible pad means having a thickness of between about ⅛ and ¼ inches shaped for conforming to the bottom of a foot for placement inside of a shoe, the pad means having a heel portion and a toe portion, the heel portion located cooperable with the heel of a user;
sensor means encased within the heel portion of the pad mans to be located beneath the heel of the user, the sensor means comprising a thin, rigid rectangular stainless steel plate means and a foil strain gage means coupled therebeneath, the plate means having a thickness of about 0.20 inches plus or minus 10% and two opposed exterior edges which are turned downwardly to for two support peripheral edges with two opposed unsupported peripheral edges therebetween thereby providing means for minimizing deflection of the plate means about an axis extending from one opposed edge to the other;
electronic module means remotely positioned from the sensor means and removably couplable to the body of the user for receiving signals from the foil sensor means, wherein the electronic module means comprises means for signaling the user to a prescribed level of weight bearing by at least one of the following methods: vibration, sound, light, continual analog and digital; and
electrical line means extending to exterior of the pad means between the sensor means and the electronic module means, the electrical line means being removably coupled to both the sensor means and electronic module means.

20. The improved orthopedic weight monitor set forth in claim 19, wherein the pad means is incorporated in a cast.

21. The improved orthopedic weight monitor set forth in claim 19, wherein the pad means is incorporated in a splint.

22. A method of providing improved orthopedic weight monitoring for the detection of weight bearing on a lower extremity for medical purposes, comprising, in combination, the steps of:
providing a flexible pad means shaped for conforming to the bottom of a foot for placement inside of a shoe, the pad means having a heel portion and toe portion positionable beneath the heel of a user;
monitoring sense means encased within the heel portion of the pad means to be located beneath the heel of the user, the sensor means comprising a thin, rigid rectangular plate means with opposed edges which minimize deflection of the plate means about an axis extending from one opposed edge to the other and having a foil strain gage means coupled therebeneath;
providing electronic module means remotely positioned from the sensor means to receive signals from the foil sensor means; and
furnishing electrical line means extending to exterior of the flexible pad means between the foil strain gage means and the electronic module means.

* * * * *